United States Patent [19]

Menart et al.

[11] Patent Number: 5,627,049

[45] Date of Patent: May 6, 1997

[54] *K. LACTIS* RP28 RIBOSOMAL PROTEIN GENE PROMOTER AND USE THEREOF

[75] Inventors: Sandrine Menart, Les Ulis; Monique Bolotin, Gif-sur-Yvette, both of France

[73] Assignee: Rhone-Poulenc Rorer S.A., Antony, France

[21] Appl. No.: 367,198

[22] PCT Filed: Jul. 6, 1993

[86] PCT No.: PCT/FR93/00695

§ 371 Date: Feb. 1, 1995

§ 102(e) Date: Feb. 1, 1995

[87] PCT Pub. No.: WO94/01570

PCT Pub. Date: Jan. 20, 1994

[30] Foreign Application Priority Data

Jul. 8, 1992 [FR] France ................................ 92 08429

[51] Int. Cl.⁶ ............................ C12P 21/06; C07H 21/04; C12N 1/00; C12N 15/63
[52] U.S. Cl. .................. 435/69.1; 435/243; 435/254.2; 435/320.1; 435/325; 435/419; 536/23.1; 536/23.2; 536/23.4; 536/23.5; 536/23.52; 536/23.72; 536/24.1

[58] Field of Search ................... 435/240.1, 243, 435/320.1, 254.11, 254.2, 69.1, 69.3, 69.5, 69.51, 69.52, 69.6, 69.7; 536/24.1, 23.1, 23.2, 23.4, 23.5, 23.52, 23.72

[56] References Cited

PUBLICATIONS

Heusterspreute et al, DNA, 1984, vol. 3(3): pp. 259–268.

*Primary Examiner*—Mindy Fleisher
*Assistant Examiner*—Terry A. McKelvey
*Attorney, Agent, or Firm*—Julie K. Smith; Martin F. Savitzky

[57] ABSTRACT

The present invention concerns DNA sequences comprising all or part of the *K.lactis* RP28 ribosomal protein promoter gene or a derivative thereof, and having transcriptional promoter activity. The invention also relates to the use of said sequences for the expression of recombinant genes.

20 Claims, 4 Drawing Sheets

K. LACTIS RP28 RIBOSOMAL PROTEIN GENE PROMOTER AND USE THEREOF

CROSS-REFERENCES TO RELATED APPLICATIONS

This application is a 371 of PCT/FR93/00695, filed Jul. 6, 1993.

BACKGROUND OF THE INVENTION

The present invention relates to the field of molecular biology. More especially, it relates to a novel DNA sequence possessing transcriptional promoter activity, to expression vectors containing this sequence and to its use for the production of recombinant proteins, and for example heterologous proteins. The invention also relates to the recombinant cells containing this DNA sequence.

The progress made in the field of molecular biology has enabled microorganisms to be modified in order to make them produce heterologous proteins. In particular, a large number of genetic studies have focused on the E.coli bacterium. However, the industrial application of these novel production methods is still limited, especially by problems of efficacy of expression of the genes in these recombinant microorganisms. Thus, with the aim of increasing the performance of these production systems, research has been carried out in order to isolate strong promoters, enabling high levels of expression of heterologous proteins to be obtained. In E.coli, the promoters of the tryptophan and lactose operons may be mentioned in particular.

More recently, in S.cerevisiae yeast, studies have focused on promoters derived from genes involved in glycolysis. There may be mentioned, in particular, the work on the 3-phosphoglycerate kinase PGK gene promoter [Dobson et al., Nucleic Acid Res. 10, 1982, 2625; Hitzeman et al., Nucleic Acid Research 1982, 7791], on that of the glyceraldehyde-3-phosphate dehydrogenase GAPDH gene [Holland et al., J.Biol.Chem. 254, 1979, 9839; Musti et al., Gene 25, 1983, 133], on that of the alcohol dehydrogenase 1 ADH1 gene [Bennentzen et al., J.Biol.Chem. 257, 1982, 3018; Denis et al., J.Biol.Chem. 25, 1983, 1165], on that of the enolase 1 ENO1 gene [Uemura et al., Gene 45, 1986, 65], on that of the GAL1/GAL10 gene [Johnston and Davis, Mol. Cell. Biol. 4 (1984) 1440] or on that of the CYC1 gene [Guarente and Ptashne, PNAS 78 (1981) 2199].

Recently, genetic tools have been developed in order to make use of Kluyveromyces yeast as a host cell for the production of recombinant proteins. The discovery of a 2-micron type plasmid originating from K.drosophilarum [plasmid pKD1-EP 241,435] has enabled a very effective host/vector system for the production of recombinant proteins to be established [EP 361,991]. However, the promoters used in this system have not been optimized up until now. In particular, the promoters in question are essentially heterologous ones, i.e. originating from other microorganisms such as, notably, S.cerevisiae. This situation can give rise to various drawbacks, and can, in particular, limit the activity of the promoter on account of the absence of certain elements of the transcriptional machinery (e.g. transactivators), exhibit some degree of toxicity for the host cell due to an absence of regulation or affect the stability of the vector.

Under these conditions, the lack of strong homologous promoters in Kluyveromyces constitutes a limiting factor in the industrial exploitation of this expression system.

SUMMARY OF THE INVENTION

The Applicant has now identified, cloned and sequenced a region of the Kluyveromyces lactis genome possessing transcriptional promoter activity (SEQ ID NO. 1). More specifically, this region corresponds to the promoter of the gene for the K.lactis ribosomal protein rp28 (Klrp28). This region, or derivatives or fragments thereof, may be used very efficiently for the production of recombinant proteins in yeasts of the genus Kluyveromyces. It is understood that this sequence may also be used in other host organisms.

Moreover, one advantage of the promoter region obtained lies in the absence of repression by glucose, which permits its use in conventional and industrial culture media.

One subject of the present invention therefore lies in a DNA sequence comprising all or part of the sequence SEQ ID. NO. 1 or of its complementary strand, or of a derivative of these sequences, and possessing a transcriptional promoter activity.

For the purposes of the present invention, derivative is understood to mean any sequence obtained from the sequence SEQ ID NO. 1 by modification(s) of genetic and/or chemical nature, conserving a promoter activity. Modification of genetic and/or chemical nature is understood to mean any mutation, deletion, substitution, addition and/or modification of one or more nucleotides. Such modifications can be carried out with various aims, and especially that of preparing portable promoters, or that of preparing promoters adapted to expression in a particular type of vector or host, that of reducing the size, of increasing the transciption promoter activity, of generating inducible promoters, of improving the level of regulation, or alternatively of changing the nature of the regulation. Such modifications can be carried out for example by mutagenesis in vitro, by introduction of additional control elements or synthetic sequences, or by deletions or substitutions of the original control elements.

When a derivative as defined above is produced, its transcriptional promoter activity can be demonstrated in several ways, and in particular by placing under the control of the studied sequence a reporter gene whose expression is detectable. Any other technique known to persons skilled in the art can obviously be used for this purpose.

The sequences SEQ ID NOS. 1 and 2 were obtained from a fusion library between fragments of the K.lactis 2359/152 genome and the E.coli lacZ gene according to the procedure described in the examples. It is understood that persons skilled in the art can isolate this region by hybridization by means of a probe comprising all or part of the sequence SEQ ID NO. 1 or of its complementary strand. The derivatives according to the invention can theta be prepared from this sequence, as indicated in the examples.

Another subject of the invention relates to a recombinant DNA comprising a DNA sequence as defined above.

This recombinant DNA can contain, e.g., the promoter sequence SEQ ID NO. 1 or a derivative thereof, into which a restriction site is inserted, facilitating the use of this sequence as a "portable" promoter. Preferably, this recombinant DNA contains, in addition, one or more structural genes. These can be, in particular, genes encoding proteins of interest in the pharmaceutical or food industry. By way of example, there may be mentioned enzymes (such as, in particular, superoxide dismutase, catalase, amylases, lipases, amidases, chymosin, and the like), blood derivatives (such as serum albumin, alpha- or beta-globin, factor VIII, factor IX, von Willebrand's factor, fibronectin, alpha$_1$-antitrypsin, and the like), insulin and its variants, lymphokines (such as interleukins, interferons, colony stimulating factors [G-CSF, GM-CSF, M-CSF, etc.], TNF, TRF, and the like), growth factors (such as growth hormone, erythropoietin, FGF, EGF, PDGF, TGF, and the like), apolipoproteins, antigenic polypeptides for the production of vaccines (hepatitis, cytomegalovirus, Eppstein-Barr, herpes, and the like), or alternatively fusions of polypeptides such as, in particular, fusions containing an active portion fused to a stabilizing portion (e.g. fusions between albumin or albumin fragments and the virus receptor or a portion of a virus receptor [CD4, and the like]).

Still more preferably, the recombinant DNA also contains signals permitting the secretion of the product of expression of the said structural gene(s). These signals may correspond to the natural secretion signals of the protein in question, but they can be of different origin. In particular, secretion signals derived from yeast genes may be used, such as those of the killer toxin [Stark and Boyd, EMBO J. 5 (1986) 1995] or alpha pheromone [Kurjan and Herskowitz, Cell 30 (1982) 933; Brake et al., Yeast 4 (1988) S436] genes.

In a particular embodiment of the invention, the recombinant DNA forms part of an expression plasmid, which can be autonomously replicating or integrative.

In particular, autonomously replicating vectors may be obtained using sequences which replicate autonomously in the chosen host. In particular, in yeast, these can be origins of replication derived from plasmids (pKD1, 2μ, and the like) or alternatively chromosomal sequences (ARS).

The integrative vectors may be obtained, in particular, using sequences homologous to certain regions of the host genome, permitting integration of the vector by homologous recombination.

Another subject of the invention relates to the recombinant cells containing a DNA sequence as defined above.

Advantageously, the cells are chosen from yeasts, and still more preferably from yeasts of the genus Kluyveromyces. It is understood, however, that the invention covers all recombinant cells in which the promoter regions of the invention are active, whether they are eukaryotic or prokaryotic cells.

Thus, among eukaryotic cells, there may be mentioned plant cells, animal cells, yeasts or fungi. In particular, in the case of yeasts, there may be mentioned yeasts of the genus Saccharomyces, Pichia, Schwanniomyces or Hansenula. In the case of animal cells, there may be mentioned COS, CHO or C127 cells and the like. Among the fungi capable of being used in the present invention, there may be mentioned more particularly Aspergillus ssp. or Trichoderma ssp. As prokaryotic hosts, bacteria such as *Escherichia coli*, or those belonging to the genera Corynebacterium, Bacillus or Streptomyces may be used.

The transcription promoter activity of the sequences of the invention in these various hosts can be checked for example by introducing into the host cell considered a recombinant DNA comprising, under the control of the promoter sequence studied, a reporter gene whose expression can be detected in the host considered.

The recombinant cells of the invention can be obtained by any method which makes it possible to introduce a foreign DNA into a cell. This may be especially transformation, electroporation, conjugation, protoplast fusion, or any other technique known to persons skilled in the art. In the case of transformation, various procedures have been described in the prior art. In particular, it can be carried out by treating the whole cells in the presence of lithium acetate and polyethylene glycol according to the technique described by Ito et al. [J. Bacteriol. 153 (1983) 163–168], or in the presence of ethylene glycol and dimethyl sulphoxide according to the technique of Durrens et al. [Curr. Genet. 18 (1990) 7]. An alternative procedure has also been described in patent application EP 361 991. In the case of electroporation, it may be carried out according to Becker and Guarentte (in: Methods in Enzymology Vol194 (1991) 182).

Another subject of the invention relates to the use of a sequence as previously defined for the expression of recombinant genes. The DNA sequences according to the invention can indeed allow high levels of production of recombinant proteins.

Advantageously, the sequences of the invention can be used for the expression of genes encoding proteins of interest in the pharmaceutical or food industry. By way of example, the proteins listed above may be mentioned.

The present invention also makes it possible to carry out a process for producing recombinant proteins, according to which a recombinant cell as defined above is cultured and the protein produced is recovered. By way of example of a protein, the proteins listed above may be mentioned.

Preferably, the process of the invention is applicable to the production of human serum albumin or one of its molecular variants. Molecular variant of albumin is understood to mean the natural variants resulting from the polymorphism of albumin, truncated forms or any hybrid protein based on albumin.

Other advantages of the present invention will emerge on reading the examples below, which should be considered as illustrative and non-limiting.

DESCRIPTION OF THE PREFERRED EMBODIMENTS

GENERAL CLONING TECHNIQUES

Figure 1A:
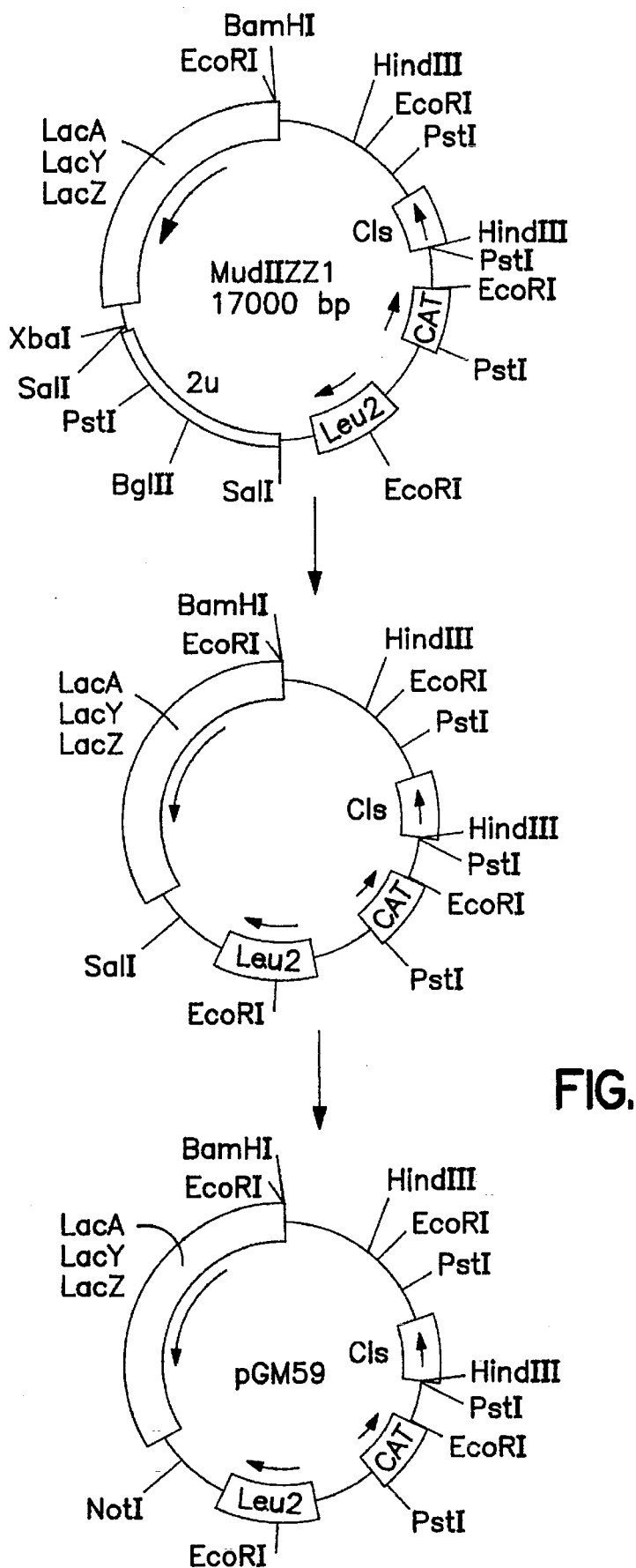
FIGS. 1A and 1B: Preparation of the transposon Mini Mu MudIIZK1.

The methods conventionally used in molecular biology, such as the preparative extractions of plasmid DNA, the centrifugation of plasmid DNA in caesium chloride gradient, electrophoresis on agarose or acrylamide gels, purification of DNA fragments by electroelution, extraction of proteins with phenol or phenol-chloroform, DNA precipitation in saline medium with ethanol or isopropanol, transformation in *Escherichia coli* and the like are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The restriction enzymes were provided by New England Biolabs (Biolabs), or Pharmacia and are used according to the recommendations of the suppliers.

The pBR322 and pUC type plasmids are of commercial origin (Bethesda Research Laboratories).

For the ligations, the DNA fragments are separated according to their size by electrophoresis on agarose or acrylamide gels, extracted with phenol or with a phenol/ chloroform mixture, precipitated with, ethanol and then incubated in the presence of phage T4 DNA ligase (Boehringer) according to the recommendations of the supplier.

The filling of the protruding 5' ends is carried out by the Klenow fragment of DNA polymerase I of *E.coli* (Boehringer) according to the specifications of the supplier. The destruction of the protruding 3' ends is carried out in the presence of phage T4 DNA polymerase (Biolabs) used according to the recommendations of the manufacturer. The destruction of the protruding 5' ends is carried out by a controlled treatment with S1 nuclease.

Site-directed mutagenesis in vitro with synthetic oligodeoxynucleotides is carried out according to the method developed by Taylor et al. [Nucleic Acids Res. 13 (1985) 8749-8764].

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335-350] is carried out using a "DNA thermal cycler" (Perkin Elmer Cetus) according to the specifications of the manufacturer.

The verification of the nucleotide sequences is carried out by the method developed by Sanger et al. [Proc. Natl. Acad. Sci. USA, 74 (1977) 5463–5467].

The transformations of *K.lactis* are carded out by any technique known to persons skilled in the art, and of which an example is given in the text.

Unless otherwise stated, the bacterial strains used are *E.coli* DH1 (Hanahan D., J. Mol. Biol. 166 (1983) 557) or *E.coli* JM109::(Mucts) (Daignanfornier and Bolotin-Fukuhara, Gene 62 (1988) 45).

The yeast strains used belong to the budding yeasts and more particularly to yeasts of the genus Kluyveromyces. The strain *K.lactis* 2359/152 and *K.lactis* SD6 were particularly used.

The yeast strains transformed with the plasmids are cultured in erlenmeyers or in 2 l pilot fermenters (SETRIC, France) at 28° C. in rich medium (YPD: 1% yeast extract, 2% Bactopeptone, 2% glucose; or YPL: 1% yeast extract, 2% Bactopeptone, 2% lactose) with constant stirring.

EXAMPLES

I—Isolation of the *K.lactis* KIrp28 promoter

The sequence SEQ ID NO. 1 was isolated from a fusion library between fragments of the *K.lactis* 2359/152 genome and the *E.coli* lacZ gene. This example describes in (A) the preparation of the fusion library, and in (B) the selection and the characterization of a clone from this library carrying the promoter of the gene for the *K.lactis* ribosomal protein rp28.

A/Preparation of the fusion library

Figure 1B:
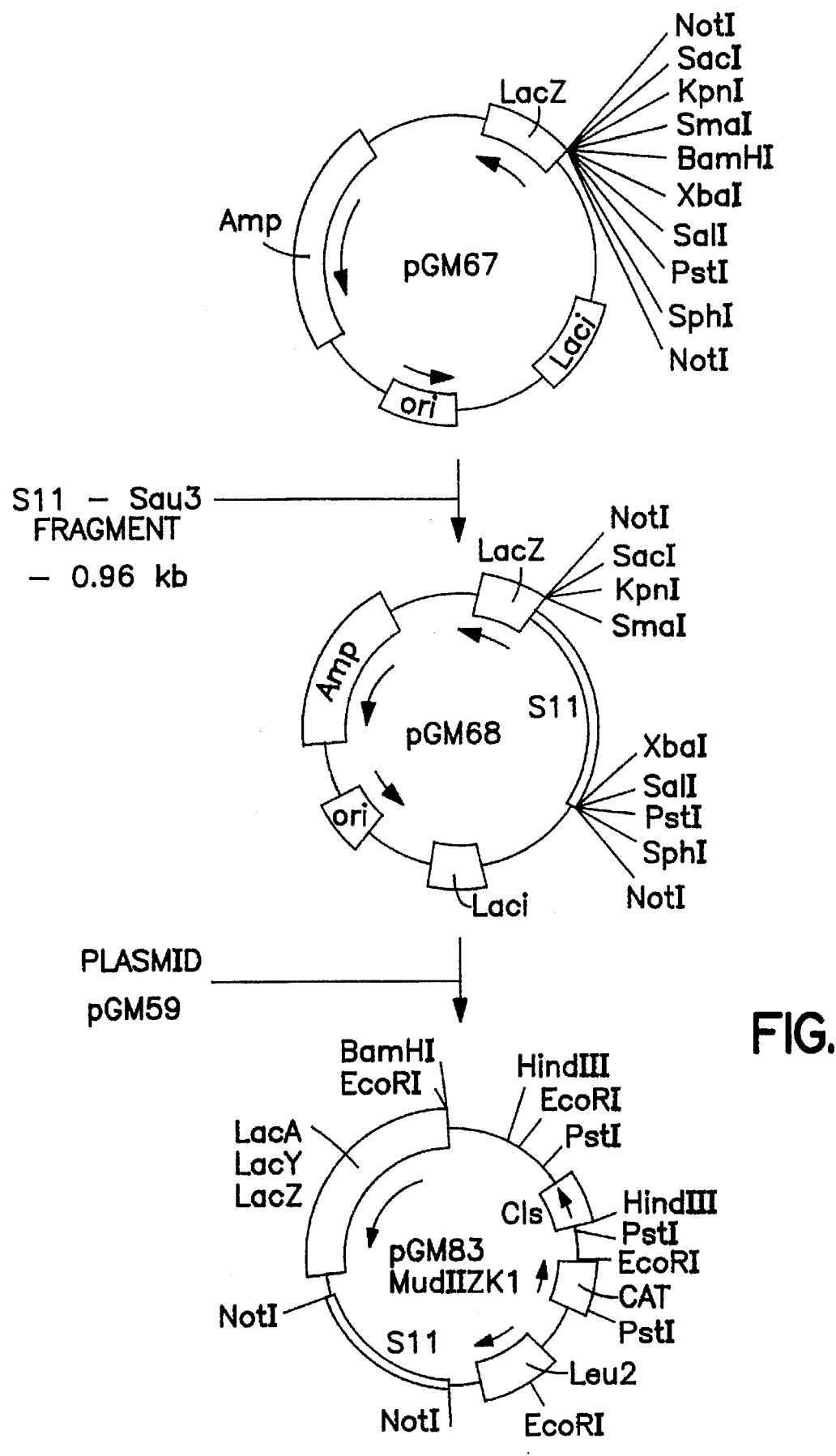
Figure 2:
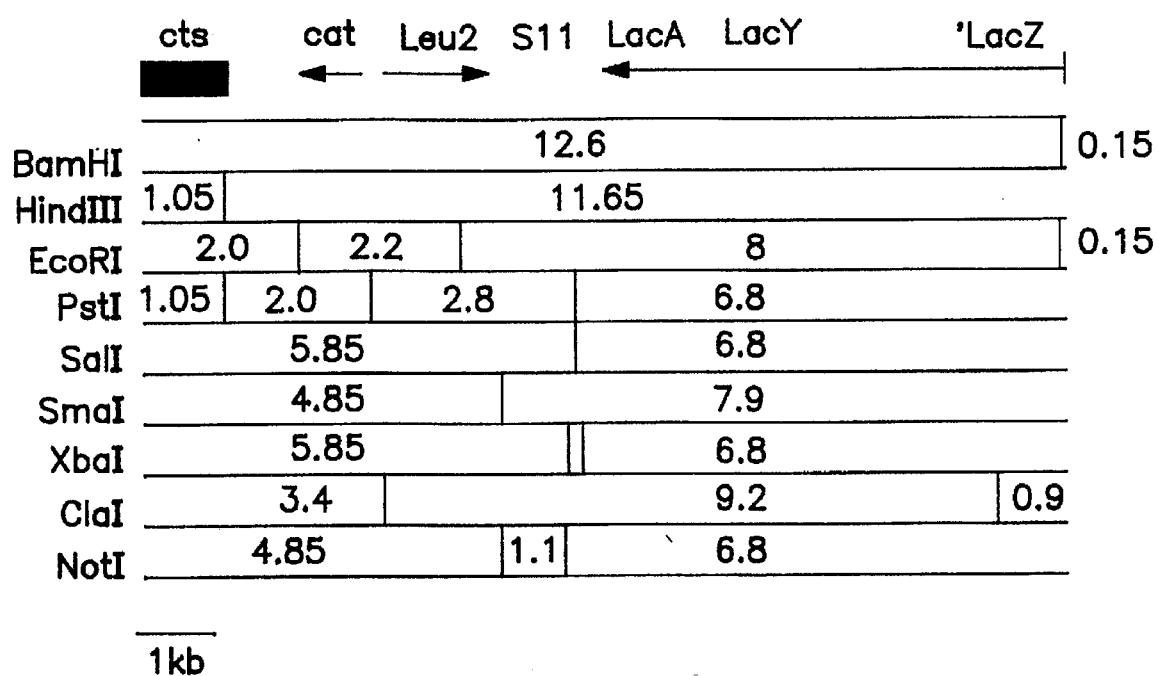
FIG. 2: Restriction map of the transposon Mini Mu MudIIZK1.

A.1. Preparation of the transposon Mini Mu MudIIZK1 (FIGS. 1 and 2).

Mini Mu MudIIZK1 was constructed from the Mini Mu MudIIZZ1 described by Daignan-Fornier and Bolotin-Fukuhara (Gene 62 (1988) 45). It was obtained by substituting the origin of replication of the mini transposon MudIIZZ1 with a replication origin which functions in Kluyveromyces: the replication origin of the plasmid pKD1 (EP 231 435).

A.1.1. Construction of a cassette carrying the origin of replication of the plasmid pKD1 (fragment S11).

In order to facilitate subsequent manipulations, the fragment S11 (carrying the origin of replication of the plasmid pKD1) was made in the form of a NotI cassette. For that, a derivative of the plasmid pUC18 was constructed in which the external sites of the multiple cloning site (HindIII and EcoRI sites) were changed to NotI sites. This was done by digestion with the corresponding enzyme, action of the Klenow enzyme and ligation with a synthetic oligonucleotide corresponding to a NotI site [oligo d(AGCGGCCGCT); SEQ ID NO: 5; Biolabs]. The plasmid obtained is designated pGM67. The fragment S11 of 960 bp obtained by digestion, with the enzyme Sau3A, of the plasmid KEp6 (Chen et al., Nucl. Acids Res. 114 (1986) 4471) was then inserted into the compatible BamHI site of the plasmid pGM67. The plasmid thus obtained, designated pGM68, contains, in the form of a NotI cassette, the fragment S11.

A.1.2. Suppression of the origin of replication 2μ of the transposon MudIIZZ1.

The plasmid pGM15 carrying the mini Mu MudIIZZ1 (Daignan-Fornier and Bolotin-Fukuhara previously cited) was deleted for the 2μ regions by digestion by means of the enzyme SalI. The unique SalI site thus obtained was then converted to a NotI site by ligation of a corresponding synthetic oligonucleotide to a NotI site after the action of the Klenow enzyme. The resulting plasmid is called pGM59.

A.1.3. Insertion of the fragment S11

The NotI cassette carrying the replication origin of the plasmid pKD1 (fragment S11), obtained from the modified plasmid pUC18, was then introduced into the unique NotI site of the plasmid pGM59.

The plasmid obtained, designated pGM83, carries a mini Mu, called MudIIZK1, which is adapted to the yeast *Kluyveromyces lactis*, as well as a functional copy of the *S.cerevisiae* LEU2 gene capable of complementing a leu2 mutation in *K.lactis* (Käimper et al, Curr. Genet. 19 (1991) 109). The restriction map of the mini-mu MudIIZK1 is represented in FIG. 2.

A.2. Introduction of the Mini Mu MudIIZK1 into the *E. coli* strain carrying the helper Mu JM109::(Mucts): Production of the strain JM109::(Mucts)::(MudIIZK1).

The strain JM109::(Mucts) was transformed with the plasmid pGM83 containing the mini mu MudIIZK1 in the presence of calcium chloride. After transformation, transposition was induced by heat shock according to the technique described by Castilho et al. (J. Bacteriol. 158 (1984) 488). The phage lysate obtained after induction is then used to superinfect the strain JM109::(Mucts). The strain JM109:: (Mucts) being recA, the linear DNA encapsulated by the phage cannot close again to give a replicative plasmid. The integrants [strain JM109::(Mucts)::(MudIIZK1)] are therefore selected as chloramphenicol-resistant ($Cm^R$), ampicillin-sensitive ($Amp^S$) clones.

A.3. Preparation of the *K.lactis* genomic library in *E.coli* DH1

High-molecular weight DNA was prepared from the *K.lactis* 2359/152 strain and partially digested with the enzyme Sau3A. The fragments of 4 to 8 kb in size were recovered on an LMP ("Low Melting Point", SEAKEM) agarose gel and cloned into the plasmid pBR322 linearized with BamHI and dephosphorylated by the action of calf intestinal phosphatase (Biolabs). 35 pools of 1000 colonies in *E. coli* DH1 were thus produced. The 1000 colonies of each pool are ampicillin-resistant and tetracyclin-sensitive, which shows that they have all inserted a *K.lactis* genomic DNA fragment in pBR322.

A.4. Preparation of the fusion library

A.4.1. Introduction of the *K.lactis* genomic library into the strain JM109::(Mucts)::(MudIIZK1).

The plasmid DNA of each pool prepared in DH1 is extracted (Maniatis). This DNA is then used to transform the strain JM109::(Mucts)::(MudIIZK1) in the presence of calcium chloride. To be representative of the 1000 colonies contained in each pool of the genomic library, more than 3000 clones per pool were recovered in the strain JM 109::(Mucts)::(MudIIZK1) permitting the transduction.

A.4.2. Transposition of the Mini Mu MudIIZK1

The fusion library is produced by extensive transposition of the Mini Mu MudIIZK1 into the plasmids forming the *K.lactis* genomic DNA library. The mini-muductions were made according to the procedure described by Castilho et al. (J. Bacteriol. 158 (1984) 488) and the transductants were selected on selective LBAC medium (LB medium (Gibco BRL) supplemented with 50 mg/l of ampicillin and 30 mg/l of chloramphenicol), the Amp$^R$ marker being provided by the plasmid, and the Cm$^R$ marker by the mini-mu. For each pool, transpositions are carried out in series, and between 10.000 and 20.000 transductants are recovered per pool. The DNA of the transductants is then extracted from a preparation of 100 ml, purified by precipitation with polyethylene glycol (Maniatis et al, 1989) and resuspended in 100 µl of water. This DNA was then used to transform *K.lactis* and to select clones carrying promoters.

B/Isolation of the *K.lactis* KIrp28 promoter

The fusion DNA prepared above was used to transform, by electroporation, a recipient *K.lactis* strain. This recipient strain, designated SD6, carries the mutations leu2 (corresponding to the mini-mu MudIIZK1 selectable marker) and lac4-8. This latter mutation prevents the strain from growing on a medium containing lactose as sole carbon source, but it can be complemented by overexpression of the *E.coli* lacZ gene encoding β-galactosidase (Chen et al., J. Basic Microbiol. 28 (1988) 211). As a result, the expression of a protein fused to β-galactosidase should permit the growth of the strain SD6 on lactose after transformation. This positive screen was used to rapidly select clones carrying strong promoters.

B.1. Construction of the recipient strain *K.lactis* SD6.

The strain SD6 (Chen et al., Mol. Gen. Genet. 233 (1992) 97) was obtained by crossing the strain *K.lactis* CXJ1-7A (a, lac4-8, ura3A, ade1-1, K1, K2, pKD1) (Chen and Fukuhara, Gene 69 (1988) 181) with the strain AWJ-137 (leu2, trp1, homothallic) (Kämper et al, Curr. Genet. 19 (1991) 109), and selecting spores having the ADE$^+$, uraA, leu2, lac4-8 genotype. Since the spores obtained were not capable of regenerating after transformation with protoplasts, a backcross was made with the strain CXJ1-7A. After mass sporulation the spores of the chosen genotype were tested by lithium chloride transformation with the plasmid KEp6 according to a technique derived from that described by Ito et al. (J. Bacteriol. 153 (1983) 163) (the LiCI concentration is 20 mM, that is to say 10 times less than that used by Ito for *S.cerevisiae*). The strain CXJ1-7A served as transformation control.

The strain SD6, selected on these criteria, transforms correctly: 1 to 3×10$^4$ transformants per µg of DNA; and the transformants have a satisfactory stability: 30 to 40% of the colonies retain the [Ura$^+$] phenotype after 6 generations in non-selective medium.

B.2. Isolation of the KIrp28 promoter

Figure 3:
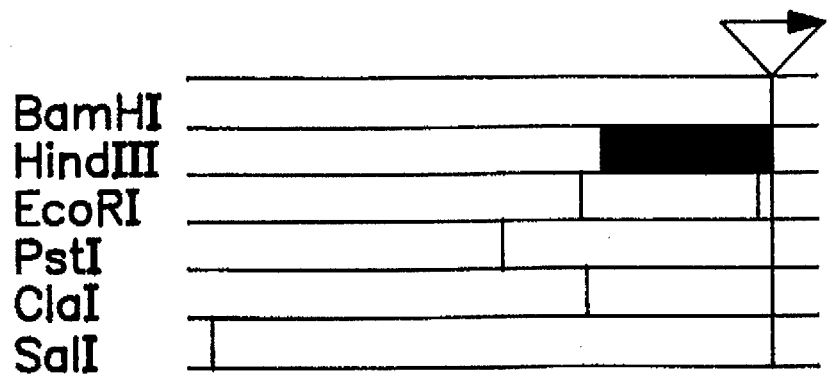
FIG. 3: Restriction map of the clone 12C10.

The strain SD6 was transformed by electroporation according to Becker and Guarante (in Methods in Enzymology vol194 (1991) 182) (Jouan apparatus; 2500 V/cm; 80–100 ng of DNNtransformation) with DNA from 11 ppols of transductants obtained in A.4.2. (corresponding to a library of 11000 clones in *E.coli*). After regenerating for 5 hours in YPD medium (yeast extract 10 g/l; peptone 10 g/l; glucose 20 g/l), the cells were, plated on lactose minimum medium. The transformants capable of growing on lactose were restreaked and, for each clone, the plasmid was extracted, amplified in *E.coli*, and, after rapid verification of the restriction map of the vector and of the mini-mu, used to retransform the yeast SD6. Among the *K.lactis* clones obtained after retransformation, one of them, the clone 12C10, was studied by restriction (see FIG. 3) and by analysis of the sequence of the junction between the *K.lactis* protein and β-galactosidase. For that, the sequence of the junction, from the lacZ end of the mini-mu (double-stranded sequence) was determined by sequencing, by means of the following oligonucleotide situated at −59 nucleotides from the junction:

5'-CTGTTTCATTTGAAGCGCG-3'(SEQ ID NO. 3)

Figure 4:
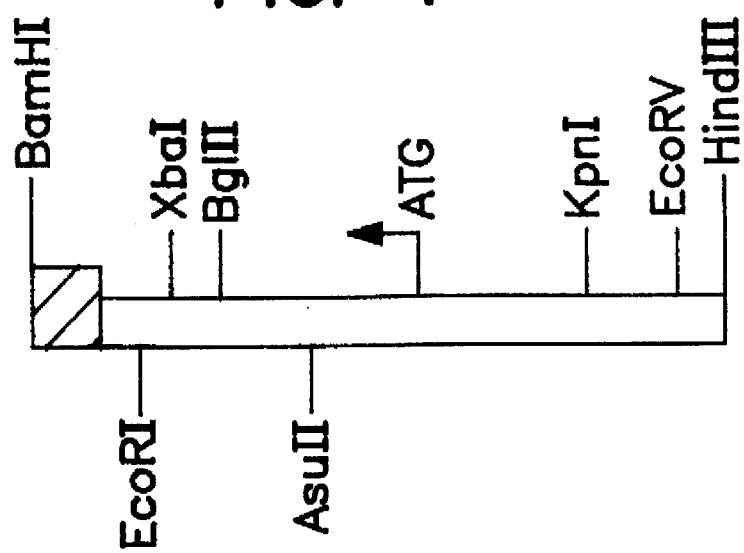
FIG. 4: Restriction map of the 1.75 kb BamHI-HindIII fragment carrying the KIrp28 promoter.

Analysis of the protein sequence deduced from the nucleotide sequence thus obtained by comparison with the sequences of protein libraries from other yeasts or eukaryotes (Genbank, MIPS, EMBL, and the like), shows that the sequence carried by the clone 12C10 corresponds to the promoter of the gene for the *K.lactis* ribosomal protein rp28. The BamHI-HindIII fragment of 1.75 kb containing the region upstream of the fusion was then subcloned into the vector Bluescript KS+ (Stratagene), a restriction map was made (FIG. 4), and the sequence was determined by sequential deletions on 0.9 kb (SEQ ID NO. 1). The production of sequence elements also makes it possible for persons skilled in the art to prepare specific probes and to reclone the promoter region of the invention by hybridization according to conventional molecular biology techniques.

II—Transformation of Kluyveromyces

Various techniques allowing the introduction of DNA into yeast can be used.

Advantageously, the various Kluyveromyces strains used were transformed by treating the whole cells in the presence of lithium acetate and polyethylene glycol, according to the technique described by Ito et al. (J. Bacteriol. 153 (1983) 163–168). The transformation technique described by Durrens et al. (Curr.Genet. 18 (1990) 7) using ethylene glycol and dimethyl sulphoxide has also been used. It is also possible to transform the yeasts by electroporation, for example according to the method described by Karube et al. (FEBS Letters 182 (1985) 90).

An alternative procedure has also been described in detail in application EP 361 991.

III—Use of the promoter of FIG. 1 for the expression of heterologous genes

The transcriptional promoter activity of the *K.lactis* region described on SEQ ID NO. 1 was detected during its very isolation, by its capacity to induce the complementation of the lac4-8 mutation of the strain SD6. This capacity results indeed from the expression of the *E.coli* lacZ gene, and thereby demonstrates the capacity for expression of heterologous genes.

IV—Construction of a portable Klrp28 promoter

A portable promoter is prepared by PCR, by insertion, into the BamHI-HindIII fragment of 1.75 kb, of a HindIII restriction site in position +1 relative to the ATG codon of the Klrp28. gene and MluI and SalI restriction sites at 533 bp upstream (SEQ ID NO. 4). The PCR product is cloned into the vector pCRII (Invitrogen) to generate the plasmid pYG177, making it possible to remove the promoter again by simple MluI-Hind-III digestion, thus facilitating the cloning into an expression vector.

A vector for expression of human serum albumin is then prepared from the plasmid pYG1018 as follows: the plasmid pYG1018 contains the prepro-albumin gene under the control of the LAC4 promoter. It is derived from the vector pYG1023 described in patent application EP 402 212, by deletion of the BssHII-MluI fragment carrying the KIPGK gene. 5 μg of the vectors pYG177 and pYG1018 are digested with 60 units of HindIII and MluI. After running on 0.8% agarose gel, the band corresponding to the rp28 promoter (about 0.5 kb), the band corresponding to the vector part (about 9 kb) and the band corresponding to the albumin cDNA (about 2 kb) are electroeluted. A 3-partner ligation (following the buffer and temperature recommendations defined by the supplier New England Biolabs) is then carried out with 1 μl of promoter DNA, 1 μl of vector DNA and 2 μl of albumin DNA. After transformation in *E.coli* (Chung et al NAR 16 (1988) 3580), the plasmid DNA from the transformants is prepared according to the SDS alkaline lysis technique of Birboim and Doly (NAR 6 (1979) 1513) modified by Ish-Horowicz and Burke (NAR 9 (1981) 2989). After enzymatic digestion, the plasmid possessing the right restricion profile is isolated. This plasmid is designated pYG183.

The strain *K.lactis* CBS 293.91 was transformed with pYG183 under the conditions described in Example II. The production of albumin by several transformants is tested according to the technique described in EP 361 991. The quantity of albumin secreted by the transform ants is similar (50–100 mg/l).

---

We claim:

1. An isolated DNA sequence selected from the group consisting of:
   (a) SEQ ID NO:4; and
   (b) a fragment of (a);
wherein said DNA sequence possesses transcriptional promoter activity.

2. A recombinant DNA comprising the isolated DNA sequence according to claim 1.

3. A recombinant DNA according to claim 2, further comprising one or more structural genes.

4. A recombinant DNA according to claim 3, further comprising signals which promote secretion of expression product(s) of said one or more structural genes.

5. A recombinant DNA according to claim 3, wherein the one or more structural genes encode proteins used in the pharmaceutical or food industries.

6. A recombinant DNA according to claim 3, wherein the one or more structural genes encode proteins selected from the group consisting of enzymes, blood derivatives, insulin, lymphokines, growth factors, apolipoproteins, antigenic polypeptides for the production of vaccines, and fusion proteins.

7. An expression plasmid comprising the recombinant DNA according to claim 2.

8. An isolated cell containing the recombinant DNA according to claim 3.

9. An isolated cell according to claim 8, wherein said cell is a yeast.

10. An isolated cell according to claim 9, wherein said cell is a yeast of the genus Kluyveromyces.

11. A process for the production of recombinant proteins, comprising culturing a cell according to claim 8 and recovering the proteins produced.

12. A process according to claim 11, wherein said proteins are used in the pharmaceutical or food industries.

13. A process according to claim 11, wherein the proteins comprise human serum albumin or a natural variant thereof.

14. A recombinant DNA according to claim 6, wherein said enzymes are selected from the group consisting of superoxide dismutase, catalase, amylases, lipases, amidases, and chymosin.

15. A recombinant DNA according to claim 6, wherein said blood derivatives are selected from the group consisting of serum albumin, alpha-globin, beta-globin, factor VIII, factor IX, von Willebrand factor, fibronectin and alpha$_1$-antitrypsin.

16. A recombinant DNA according to claim 6, wherein said lymphokines are selected from the group consisting of interleukins, interferons, colony stimulating factors, TNF, and TRF.

17. A recombinant DNA according to claim 16, wherein said colony stimulating factors are selected from the group consisting of G-CSF, GM-CSF, and M-CSF.

18. A recombinant DNA according to claim 6, wherein said growth factors are selected from the group consisting of growth hormone, erythropoietin, FGF, EGF, PDGF, and TGF.

19. A recombinant DNA according to claim 6, wherein said antigenic polypeptides are selected from the group consisting of antigens from hepatitis, cytomegalovirus, Epstein-Barr virus, and herpes virus.

20. A recombinant DNA according to claim 6, wherein said fusion proteins are comprised of a fusion between albumin or fragments of albumin and a virus receptor or fragment thereof.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 970 base pairs
        ( B ) TYPE: nucleic acid
        ( C ) STRANDEDNESS: double
        ( D ) TOPOLOGY: linear ( i i ) MOLECULE TYPE: cDNA ( i v ) ANTI-SENSE: NO ( v i ) ORIGINAL SOURCE:
        ( A ) ORGANISM: Kluyveromyces lactis ( i x ) FEATURE:
        ( A ) NAME/KEY: CDS
        ( B ) LOCATION: 883..969

( x i ) SEQUENCE DESCRIPTION: SEQ ID NO:1:

```
AAGCTTTAAT  GCGGTAGTTT  ATCACAGTTA  AATTGCTAAC  GCAGTCAGGC  ACCGTGTATG    60

AAATCTAACA  ATGCGCTCAT  CGTCATCCTC  GGCACCGTCA  CCCTGGATGC  TGTAGGCATA   120

GGCTTGGTTA  TGCCGGTACT  GCCGGGCCTC  TTGCGGGATA  TCGTCCATTC  CGACAGCATC   180

GCCAGTCACT  ATGGGTGCTG  CTAGCGCTAT  ATGCGTTGAT  GCAATTTCTA  TGCGCACCCG   240

TTCTCGGAGC  ACTGTCCGAC  CGCTTTGGCC  GCCGCCCAGT  CCTGCTCGCT  TCGCTACTTG   300

GAGCCACTAT  CGACTACGCG  ATCATGGCGA  CCACACCCTG  TCCTGTGGAT  CAATAGAAGG   360

GTTCAACCAT  TTCATCATTT  TTGTTTCTGT  ATTGATGTTG  TGCGGAAGTA  TATGTTATGT   420

GATTTCCAGG  TACCTCTCTG  TAGGAGCCAA  GTTTGTAAAA  TTTTAGGTCT  ACTGGCAGCA   480

TAACTAAACG  GAAACATATT  CACACTTATA  TCCAATATAT  ATATGTACAT  GATATAATTG   540

ACAGATTTTA  ACTGTTGATC  GTCAGTCTGA  TGTGATGACA  CTGTCACTGG  ACAGAAGCCG   600

AACACAGGTC  ACATGACTAA  CATATGTTTT  CTGGGACTGT  TTGAGAATGT  ACGGATGTAG   660

TTTTTTCAAA  ACTAGAAAAC  CAACAATATA  TTACCTAAAT  AGGAATAAAG  TTTTCAAAAC   720

TCATCAACTC  ACTGACATCG  ACAAATTTCA  CATCGTTACG  AGTAGTGCAT  ATATGAAGAA   780
```

```
ACCATCTTTC AATACAGTTA ATCATACCAT TAAGCATATG TTCTAATGTA CTATTATCTC        840

GATTAATTCT TGAAAGAACA CACACAATAA GCAAGTCTCA AA ATG GGT ATT GAT           894
                                             Met Gly Ile Asp
                                               1

CAC ACT TCC AAG CAA CAC AAG AGA TCC AGT CAC AGA ACT GCT CCA AAG          942
His Thr Ser Lys Gln His Lys Arg Ser Ser His Arg Thr Ala Pro Lys
 5               10                  15                      20

TCC GAC AAC GTC TAC TTG AAG TTG TTG G                                    970
Ser Asp Asn Val Tyr Leu Lys Leu Leu
                 25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Ile Asp His Thr Ser Lys Gln His Lys Arg Ser Ser His Arg
 1               5                  10                      15

Thr Ala Pro Lys Ser Asp Asn Val Tyr Leu Lys Leu Leu
             20                  25
```

( 2 ) INFORMATION FOR SEQ ID NO:3:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid ( i v ) ANTI-SENSE: NO ( x i ) SEQUENCE DESCRIPTION: SEQ ID NO:3:

```
CTGTTTCATT TGAAGCGCG                                                      19
```

( 2 ) INFORMATION FOR SEQ ID NO:4:

( i ) SEQUENCE CHARACTERISTICS:
        ( A ) LENGTH: 549 base pairs
        ( B ) TYPE: nucleic acid
        ( C ) STRANDEDNESS: double
        ( D ) TOPOLOGY: linear ( i i ) MOLECULE TYPE: cDNA ( i v ) ANTI-SENSE: NO ( x i ) SEQUENCE DESCRIPTION: SEQ ID NO:4:

```
ACGCGTGTCG ACGATCAATA GAAGGGTTCA ACCATTTCAT CATTTTGTT TCTGTATTGA          60

TGTTGTGCGG AAGTATATGT TATGTGATTT CCAGGTACCT CTCTGTAGGA GCCAAGTTTG        120

TAAAATTTTA GGTCTACTGG CAGCATAACT AAACGGAAAC TATTCACACT TATATCCAAT        180

ATATATATGT ACATGATATA ATTGACAGAT TTAACTGTT GATCGTCAGT CTGATGTGAT         240

GACACTGTCA CTGGACAGAA GCCGAACACA GGTCACATGA CTAACATATG TTTTCTGGGA        300

CTGTTTGAGA ATGTACGGAT GTAGTTTTTT CAAAACTAGA AAACCAACAA TATATTACCT        360

AAATAGGAAT AAAGTTTTCA AAACTCATCA ACTCACTGAC ATCGACAAAT TCACATCGT         420

TACGAGTAGT GCATATATGA AGAAACCATC TTTCAATACA GTTAATCATA CCATTAAGCA        480
```

```
TATGTTCTAA TGTACTATTA TCTCGATTAA TTCTTGAAAG AACACACACA ATAAGCAAGT        540

CTCAAGCTT                                                                549
```

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:5:

```
AGCGGCCGCT                                                                10
```